(12) United States Patent
Qiao et al.

(10) Patent No.: US 6,797,393 B2
(45) Date of Patent: Sep. 28, 2004

(54) METHOD FOR MAKING BIOCHIP SUBSTRATE

(75) Inventors: Tiecheng A. Qiao, Webster, NY (US); Krishnan Chari, Fairport, NY (US); Thomas L. Penner, Fairport, NY (US); Zhihao Yang, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 59 days.

(21) Appl. No.: 10/020,747

(22) Filed: Nov. 30, 2001

(65) Prior Publication Data

US 2003/0138649 A1 Jul. 24, 2003

(51) Int. Cl.$^7$ ................................................ B32B 9/02
(52) U.S. Cl. ................................... 428/478.2; 427/2.13
(58) Field of Search ....................... 428/478.2; 427/2.13

(56) References Cited

U.S. PATENT DOCUMENTS

| | | | |
|---|---|---|---|
| 5,110,833 A | | 5/1992 | Mosbach |
| 5,977,322 A | * | 11/1999 | Marks et al. .......... 530/388.85 |
| 5,981,734 A | | 11/1999 | Mirzabekov et al. |
| 2001/0041339 A1 | | 11/2001 | Anderson et al. |

FOREIGN PATENT DOCUMENTS

| | | |
|---|---|---|
| EP | 98/08086 | 2/1998 |
| EP | 1 106 603 A2 | 6/2001 |
| WO | WO 95/041594 | 2/1995 |
| WO | WO 98/29736 | 7/1998 |
| WO | WO 00/04382 | 1/2000 |
| WO | WO 00/04389 | 1/2000 |
| WO | WO 01/04312 | 6/2001 |
| WO | WO 01/40803 | 6/2001 |

OTHER PUBLICATIONS

Kirk–Othmer Encyclopedia of Chemical Technology, John Wiley & Sons, Inc.: 1994; online posting date Dec. 2000, introduction and sections 3, 4.*
*Anal. Biochem*, (2000) 278, 123–131.
*Using Antibodies; A Laboratory Manual*, Cold Spring Harbor Laboratory Press, by Ed Harlow and David Lane, Cold Spring Harbor, NY 1999, pp 3–99.
*Science*, vol. 249, 505–510, 1990.
*Nature*, vol. 346, 818–822, 1990.
*Chem. Rev.* vol. 100, 2495–2504, 2000.
P.I. Rose, "The Theory of the Photographic Process", 4$^{th}$ Edition, T.H. James ed. pp. 51 to 67.
Edgar B. Gutoff in Chapter 1 of "Modern Coating And Drying Technology", (Interfacial Engineering Series; v. 1), (1992), VCH Publishers Inc., New York, NY.

* cited by examiner

*Primary Examiner*—James J. Seidleck
*Assistant Examiner*—Melanie Bissett
(74) *Attorney, Agent, or Firm*—Kathleen Neuner Manne

(57) ABSTRACT

A gelatin-based substrate for fabricating protein arrays, the substrate containing: gelatin and a trifunctional compound A—L—B; wherein A is a functional group capable of interacting with the gelatin; L is a linking group capable of interacting with A and with B; and B is a functional group capable of interacting with a protein capture agent. A may be the same or different from B.

18 Claims, No Drawings

METHOD FOR MAKING BIOCHIP SUBSTRATE

FIELD OF THE INVENTION

The present invention relates to fabricating protein microarrays in general and in particular to a method that utilizes a gelatin-based substrate wherein the gelatin surface is modified to improve specific attachment of biological molecules.

BACKGROUND OF THE INVENTION

The completion of Human Genome project spurred the rapid growth of a new interdisciplinary field of proteomics which includes: identification and characterization of complete sets of proteins encoded by the genome, the synthesis of proteins, post-translational modifications, as well as detailed mapping of protein interaction at the cellular regulation level.

While 2-dimensional gel electrophoresis in combination with mass spectrometry still remains the dominant technology in proteomics study, the successful implantation and application of DNA microarray technology to gene profiling and gene discovery have prompted scientists to develop protein microarray technology and apply microchip based protein assays to the field of proteomics. For example, in WO 00/04382 and WO 00/04389, a method of fabricating protein microarrays is disclosed. A key element in the disclosure is a substrate consisting of a solid support coated with a monolayer of thin organic film on which protein or a protein capture agent can be immobilized.

Nitrocellulose membrane was widely used as a protein blotting substrate in Western blotting and enzyme linked immunosorbent assay (ELISA). In WO 01/40312 and WO 01/40803, antibodies are spotted onto a nitrocellulose membrane using a gridding robot device. Such spotted antibody microarrays on a nitrocellulose membrane substrate have been shown to be useful in analyzing protein mixture in a large parallel manner.

In WO 98/29736, L. G. Mendoza et al. describe an antibody microarray with antibody immobilized onto a N-hydroxysuccinimidyl ester modified glass substrate. In U.S. Pat. No. 5,981,734 and WO 95/04594, a polyacrylamide based hydrogel substrate technology is described for the fabrication of DNA microarrays. More recently, in *Anal. Biochem.* (2000) 278, 123–131, the same hydrogel technology was further demonstrated as useful as a substrate for the immobilization of proteins in making protein microarrays.

In the above cited examples, the common feature among these different approaches is the requirement of a solid support that allows covalent or non-covalent attachment of a protein or a protein capture agent on the surface of said support. In DNA microarray technology, a variety of surfaces have been prepared for the deposition of pre-synthesized oligos and PCR prepared cDNA probes. However, unlike DNA, proteins tend to bind to surfaces in a non-specific manner and, in doing so, lose their biological activity. Thus, the attributes for a protein microarray substrate are different from those for a DNA microarray substrate in that the protein microarray substrate must not only provide surface functionality that are capable of interacting with protein capture agents, but must also resist non-specific protein binding to areas where no protein capture agents have been deposited.

Bovine serum albumin (BSA) has been demonstrated to be a useful reagent in blocking proteins from non-specific surface binding. Polyethylene glycol and phospholipids have also been used to passivate surfaces and provide a surface resistant to non-specific binding. However, all of these methods suffer disadvantages either because surface preparation takes a long time or because the method of surface modification is complex and difficult, making the method less than an ideal choice for large scale industrial manufacture.

Hence, there is still need to discover other low cost and readily manufacturable materials that serve as a matrix on a solid support for the attachment of protein capture agents. The art needs a substrate with chemical functionality for the immobilization of protein capture agents, but such substrate must not bind proteins to areas on the gelatin surface that are without immobilized protein capture agents.

SUMMARY OF THE INVENTION

The present invention seeks to solve some of the problems discussed above by providing:

A gelatin-based substrate for fabricating protein arrays, the substrate comprising: gelatin and a trifunctional compound A—L—B; wherein A is a functional group capable of interacting with the gelatin; L is a linking group capable of interacting with A and with B; and B is a functional group capable of interacting with a protein capture agent, wherein A may be the same or different from B.

Also provided is a method of making a gelatin-based substrate for fabricating protein arrays comprising the steps of providing a support; coating on the support a composition containing gelatin; and affixing to a surface of the gelatin a trifunctional compound A—L—B; wherein A is a functional group capable of interacting with the gelatin; L is a linking group capable if interacting with A and with B; and B is a functional group capable of interacting with a protein capture agent; wherein A may be the same or different from B.

The invention is particularly useful in fabricating protein microarrays. The invention provides a gelatin substrate with at least one surface to which certain functionalities have been affixed. Thus treated, or modified, the gelatin surface is substantially resistant to non-specific binding. Further, the functionalities are capable of interacting specifically with protein capture agents with which they come in contact. Thus, the substrate of the invention affords a high degree of specific binding between the modified gelatin surface and protein capture agents.

Gelatin substrates that have been modified according to this invention require a very low concentration of biological sample in fabricating protein microarrays when compared with unmodified gelatin substrates. Also, the gelatin substrates of the invention can be readily manufactured at low cost. The usefulness of the claimed substrate for protein attachment is demonstrated below in the examples, using several chemical modification methods and enzyme linked immunosorbent assay (ELISA).

DETAILED DESCRIPTION OF THE INVENTION

In general, a protein microarray can be prepared by first modifying a solid support, namely the protein microarray support, followed by depositing various protein capture agents onto the modified substrate at pre-defined locations. Supports of choice for protein microarray applications can be organic, inorganic or biological. Some commonly used support materials include glass, plastics, metals, semiconductors. The support can be transparent or opaque, flexible or rigid. In some cases, the support can be a porous membrane e.g. nitrocellulose and polyvinylidene difluoride, and the protein capture agents are deposited onto the membrane by physical adsorption. However, to improve robustness and reproducibility, it is more desirable to immobilize the protein capture agents onto a substrate through chemical covalent bond.

To immobilize protein capture agents onto a solid support, the support needs to be modified by certain chemical functional agents. In general, the chemically functional agent is a bi-functional molecule which can be represented as A—L—B, in which A and B are chemical functionalities that are capable of reacting or interacting with gelatin and protein capture agent molecules to be immobilized on the substrate and L is linkage group. Preferably, L is a diradical of such a length that the shortest through—bond path between the ends that connect A to B is not greater than 10 atoms.

There are two classes of bi-functional agents: 1). homofunctional agent if A=B; and 2). heterofunctional agent if A≠B. Some commonly used A and B include but are not limited to, aldehyde, epoxy, hydrazide, vinyl sulfone, succinimidyl ester, carbodiimide, maleimide, dithio, iodoacetyl, isocyanate, isothiocyanate, aziridine. The linking group L comprises any reasonable combination of relatively non-labile covalently bonded chemical units sufficient to connect the two functionalities A and B. These chemical units can consists of, but are not necessarily limited to, a single bond, a carbon atom, an oxygen atom, a
sulfur atom, a carbonyl group

a carboxylic ester group

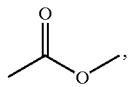

a carboxylic amide group

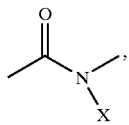

a sulfonyl group

a sulfonamide group

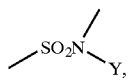

an ethyleneoxy group, a polyethyleneoxy group, or an amino group

where substituents X, Y, and Z are each independently a hydrogen atom, or an alkyl group of 1–10 carbon atoms; and linear or branched, saturated or unsaturated alkyl group of 1 to 10 carbon atoms (such as methyl, ethyl, n-propyl, isopropyl, t-butyl, hexyl, decyl, benzyl, methoxymethyl, hydroxyethyl, iso-butyl, and n-butyl); a substituted or unsubstituted aryl group of 6 to 14 carbon atoms (such as phenyl, naphthyl, anthryl, tolyl, xylyl, 3-methoxyphenyl, 4-chlorophenyl, 4-carbomethoxyphenyl and 4-cyanophenyl); and a substituted or unsubstituted cycloalkyl group of 5 to 14 carbon atoms such as cyclopentyl, cyclohexyl, and cyclooctyl); a substituted or unsubstituted, saturated or unsaturated heterocyclic group (such as pyridyl, primidyl, morpholino, and furanyl); a cyano group. Some solubilizing groups can also be introduced into A—L—B and examples of these solubilizing groups include, but are not limited to, carboxylic acid, sulfonic acid, phosphonic acid, hydroxamic acid, sulfonamide, and hydroxy groups (and their corresponding salts). A and B can also be in the form of readily reactive functionalities towards crosslinkers, examples include but not limited to carboxy, amino, and chloromethyl, etc. A and B can be affinity tags that are capable of interacting non-covalently with the protein capture agents intended to be immobilized onto the substrate. For example, some commonly used tag systems include, but are not limited to, streptavidin and biotin, histidine tags and nickel metal ions, glutathione-S-transferase and glutathione. One skilled in the art should be able to create a fusion protein capture agent using recombination DNA technology and an element of tag recognition unit can be introduced into protein capture agent in this way.

Once a protein microarray substrate is modified, protein capture agents will be placed onto the substrate to generate protein microarray content. Protein capture agents are molecules which can interact with proteins in high affinity and high specificity. Typically it is desirable to have an affinity binding constant between a protein capture agent and target protein greater than $10^6$ $M^{-1}$. There are several classes of molecules that can be used as protein capture agents on a protein microarray. Antibodies are a class of naturally occurring protein molecules that are capable of binding targets with high affinity and specificity. The properties and protocols of using antibody can be found in "*Using Antibodies; A Laboratory Manual*", (Cold Spring Harbor Laboratory Press, by Ed Harlow and David Lane, Cold Spring Harbor, N.Y. 1999). Antigens can also be used as protein capture agents if antibodies are intended targets for detection. Protein scaffolds such as whole protein/enzyme or their fragments can be used as protein capture agents as well. Examples include phosphotases, kinases, proteases, oxidases, hydrolyases, cytokines, or synthetic peptides. Nucleic acid ligands can be used as protein capture agent molecules after in vitro selection and enrichment for their binding affinity and specificity to certain targets. The principle of such selection process can be found in *Science*, Vol. 249, 505–510, 1990 and *Nature*, Vol. 346, 818–822, 1990. U.S. Pat. No. 5,110,833 discloses an alternative class of synthetic molecules that can mimic antibody binding affinity and specificity and can be readily prepared by the so called Molecular Imprinting Polymer (MIP). This technology has been reviewed in *Chem. Rev. Vol.* 100, 2495–2504, 2000.

In practice, a protein microarray is brought into contact with a biological fluid sample, proteins in the sample will adsorb to both areas spotted with specific protein capture agents and areas without protein capture agents. Since the protein microarray is intended to be used for the measurement of specific interactions between protein capture agents on the chip with certain proteins or other molecules in the biological fluid sample, the non-specific binding of sample proteins to non-spotted area would give rise to high background noise. The term non-specific binding refers to the tendency of protein molecules to adhere to a solid surface in a non-selective manner. This high background noise resulting from the non-specific binding will interfere with reporter signals to be detected from the spotted area unless the non-specific binding is blocked in an appropriate manner. Typically, the protein microarray will be immersed in a solution containing a blocking agent to block the non-specific binding sites before its contact with the intended analyte solution. A commonly used method for blocking protein non-specific binding is to treat the surface of the substrate with a large excess of bovine serum albumin. The non-spotted surface area may also be chemically modified with polyethylene glycol (PEG), phospholipid, or poly lysine to prevent non-specific binding.

Gelatin has been used in the photographic industry as a binder for various chemical components, and the process of making high quality gelatin is well established in industry. Because gelatin is made of biological materials, it is biologically compatible with protein capture agents on the protein microarray. The gelatin coated surface provides a biologically benign surface for the immobilization of protein capture agents onto the protein microarray. As shown in this invention, gelatin also renders a surface that substantially reduce background noise that is a result of non-specific binding. Normally, gelatin is coated onto a substrate and gelation occurs through a process by which gelatin solutions or suspensions of gelatin and other materials form continuous three-dimensional networks that exhibit no steady state flow. This can occur in polymers by polymerization in the presence of polyfunctional monomers, by covalent cross-linking of a dissolved polymer that possesses reactive side chains and by secondary bonding, for example, hydrogen bonding, between polymer molecules in solution. Polymers such as gelatin exhibit thermal gelation which is of the latter type. The process of gelation or setting is characterized by a discontinuous rise in viscosity. (See, P. I. Rose, "The Theory of the Photographic Process", $4^{th}$ Edition, T. H. James ed. pages 51 to 67).

The gelatin substrate described in this invention can either be coated as is on any solid support, or with one or a combination of multiple hardening agents mixed in the gel. The level of the hardening agent should be from 0 to 20 wt. %, and preferably 0.5 to 8 wt. %, of the total gelatin coated.

There are two types of gelatin: acid pretreated and alkaline pretreated. The preferred gelatin is alkaline pretreated gelatin from bovine bone marrow, but gelatin can also come from other sources. Examples include, but are not limited to, pig gelatin, fish gelatin. The bi-functional agent A—L—B can be introduced either during or after the gelatin coating onto a solid support.

Coating methods are broadly described by Edward Cohen and Edgar B. Gutoff in Chapter 1 of "Modern Coating And Drying Technology", (Interfacial Engineering Series; v.1), (1992), VCH Publishers Inc., New York, N.Y. In general, a fluid coating composition contains a binder, a solvent to dissolve or suspend the components, and optional additives such as surfactants, dispersants, plasticizers, biocides, cross-linking agents for toughness and insolubility, and conductive materials to minimize static buildup. All the components are mixed and dissolved or dispersed, and the coating fluid is sent to an applicator where it is applied to a substrate by one of several coating techniques. Heat is then applied to the coating to evaporate the solvent and produce the desired film, or the coating is solidified by the action of ultraviolet radiation or an electron beam.

The most suitable coating method—including the coating speed—will depend on the quality and functionality desired and the materials being used, e.g., the substrate, the solvent, weight and viscosity of the coating, etc. For a single layer format, suitable coating methods may include dip coating, rod coating, knife coating, blade coating, air knife coating, gravure coating, forward and reverse roll coating, and slot and extrusion coating.

Coating speed can also be an important determinant in the choice of coating method. Although most methods can be used at low speeds, and all methods have a limiting upper speed, some work better at higher speeds. Curtain coating requires a minimum flow to maintain the integrity of the curtain. Therefore, this method is limited to higher speeds id a thin coating is to be obtained. In slide coating of multiple layers, interfacial instabilities are more likely to occur on the slide when the layers are very thin. Higher speeds, with their higher flows and thicker layers on the slide, tend to avoid these instabilities. See, p. 12, "Modern Coating and Drying Technology", supra.

The gelatin has a laydown of 0.2 to 100 grams per square meter; preferably 10 to 50 grams per square meter.

Any well known coating method, such as bead coating or curtain coating, can be used to prepare the gelatin substrate. The gelatin could be coated with any other coating aids such as surfactants and thickeners to adjust its physical property. The gelatin used in the invention may be chemically modified either before, during or after the coating process to create more chemical functionalities that can react or interact with biologically active molecules or assemblies intended to be attached on this substrate.

The invention can be better appreciated by reference to the following specific embodiments.

EXAMPLES

Example 1

This example illustrates the formulation of gelatin melt and the method of coating the melt onto a reflective support.

Formulation 1-1

This was prepared by adding 3.0 grams of Type IV gelatin in 9.1 grams of water, 0.032 grams of coating aid of Nonylphenoxypolyglycerol in 0.3 grams of water, 0.06 grams of coating aid Sodium octyl phenol poly (etheneoxy) sulfonate in 0.8 grams of water, 0.15 grams of Ethene, 1,1'-(methylenebis(sulfonyl))bis-in 8.25 grams water and 98.3 grams of distilled water.

Formulation 1-2

This was prepared by adding 3.0 grams of Type IV gelatin in 9.1 grams of water, 0.032 grams of coating aid Nonylphenoxypolyglycerol in 0.3 grams of water, 0.06 grams of coating aid Sodium octyl phenol poly (etheneoxy) sulfonate in 0.8 grams water, 0.30 grams of Ethene, 1,1'-(methylenebis(sulfonyl))bis-in 16.5 grams water and 89.9 grams of distilled water.

Formulation 1-3

This was prepared by adding 3.0 grams of Type IV gelatin in 9.1 grams of water, 0.032 grams of coating aid Nonylphenoxypolyglycerol in 0.3 grams of water, 0.06 grams of coating aid Sodium octyl phenol poly (etheneoxy) sulfonate in 0.8 grams water, 0.45 grams of Ethene, 1,1'-(methylenebis (sulfonyl))bis-in 24.75 grams water and 81.5 grams of distilled water.

Formulation 1-4

This was prepared by adding 3.0 grams of Type IV gelatin in 9.1 grams of water, 0.032 grams of coating aid Nonylphenoxypolyglycerol in 0.3 grams of water, 0.06 grams of coating aid Sodium octyl phenol poly (etheneoxy) sulfonate in 0.8 grams water, 0.60 grams of Ethene, 1,1'-(methylenebis (sulfonyl))bis-in 32.9 grams water and 73.2 grams of distilled water.

Formulation 1-5

This was prepared by adding 3.0 grams of Type IV gelatin in 9.1 grams of water, 0.032 grams of coating aid Nonylphenoxypolyglycerol in 0.3 grams water, 0.06 grams of coating aid Sodium octyl phenol poly (etheneoxy) sulfonate in 0.8 grams water, 0.75 grams of Ethene, 1,1'-(methylenebis (sulfonyl))bis-in 41.15 grams of water and 64.8 grams of distilled water.

Formulations 1-1 to 1-5 were coated on a reflective photographic paper substrate using a coating device. The formulations were introduced through a slot coating die at a temperature of 45° C. onto a 12.7 cm wide web moving at the rate of 3.7 m/min. The flow rate was adjusted to provide a level of 86.1 g/m² gelatin coverage. The coatings were chill-set in a 2.4 m long chilling section that was maintained at a temperature of 4° C. and 56.6% RH and then dried in two drying sections that were 9.8 m and 11.6 m in length respectively. The first drying section was maintained at a temperature of 21° C. and 33.2% RH and the second was maintained at a temperature of 37.8° C. and 18.6% RH.

Example 2

This example illustrates the method of evaluating gelatin coating using a modified enzyme linked immunosobent assay (ELISA).

The Procedure to Perform the Modified ELISA is as Follows

1. Goat anti-mouse antibody IgG from Sigma was dissolved in PBS (phosphate saline buffer, pH7.4) buffer to a concentration of 1 mg/mL. A series of diluted of goat anti-mouse antibody IgG was spotted manually onto nitrocellulose membrane and coated gelatin substrates. The spotted substrates were incubated in a humid chamber for 1 hour at room temperature.
2. The substrates were washed four times in PBS buffer with 1% Triton X100™, 5 min each time with shaking.
3. The washed substrates were incubated in PBS buffer with 1% glycine for 15 min with constant shaking.
4. The substrates were washed four times in PBS buffer with 1% Triton™ X100 with shaking.
5. Mouse IgG from Sigma was diluted in PBS buffer with 0.1% Tween™ 20 to 1 μg/mL to cover the whole surface of substrates, and the substrates were incubate at room temperature for 1 hour.
6. The substrates were washed four times with PBS buffer with 1% Triton X100™, 5 min each time with constant shaking.
7. The substrates were incubated in goat anti-mouse IgG horse radish peroxidase conjugate (diluted in PBS with 1% glycine to appropriate titer) solution to cover the whole surface of the substrates at room temperature for 1 hour with shaking.
8. The substrates were washed four times with PBS buffer with 1% Triton X100™, 5 min each time with constant shaking, and rinsed twice in water.
9. The color were developed in horse radish peroxidase substrate solution containing 3,3'-diaminobenzidine tetrahydrochloride (DAB) from Sigma following manufacture's recommendation.

The substrates with color developed on their surfaces were air-dried and the reflection densities of the spotted area and non-spotted area were measured on a Perkin-Elmer PDS microdensitometer with Status 'A' filtration. The data are shown in Table 1.

| Sample ID | BVSM level vs total gelatin | Spot density with 100 ng of goat anti-mouse IgG | Spot density with 75 ng of goat anti-mouse IgG | Spot density with 50 ng of goat anti-mouse IgG | Spot density with 0 ng of goat anti-mouse IgG, background density | Comments |
|---|---|---|---|---|---|---|
| Nitrocellulose membrane | N/A | 0.86 | 0.74 | 0.60 | 0.41 | Comparative |
| 1-1 | 2% | 0.36 | 0.17 | 0.13 | 0.10 | Invention |
| 1-2 | 4% | 0.50 | 0.27 | 0.20 | 0.11 | Invention |
| 1-3 | 6% | 0.52 | 0.35 | 0.26 | 0.12 | Invention |
| 1-4 | 8% | 0.55 | 0.38 | 0.28 | 0.12 | Invention |
| 1-5 | 10% | 0.56 | 0.40 | 0.30 | 0.12 | Invention |

Background densities are caused by non-specific protein binding to the surface of the substrate. The results show that all five inventive examples gave much lower background densities than the control sample on nitrocellulose membrane.

Example 3

This example illustrates the modification of coated gelatin using homobifunctional crosslinkers to improve its surface protein binding capacity. 3-1: Gelatin was coated according to Example 1 and the coating was immersed in 0.01 M phosphate buffer pH7.0 containing 1.25% glutaraldehyde. The reaction was allowed to proceed for 3 hours at room temperature and the coating was rinsed with water. The resultant Schiff base was reduced by using a 10 mg/mL sodium borohydride solution. The coating was washed with distilled water and air-dried. Goat anti-mouse antibody was spotted onto such treated substrate and evaluated as described in Example 2.

3-2: Gelatin was coated according to Example 1 and the coating was immersed in 0.01 M phosphate buffer pH7.0 containing 10 mM bis(sulfosuccinimidyl) suberate. The reaction was allowed to proceed for 1 hour at room temperature and the coating was rinsed with distilled water and air-dried. Goat anti-mouse antibody was spotted onto such treated substrate and evaluated as described in Example 2.

3-3: Gelatin was coated according to Example 1 and the coating was immersed in 0.01 M phosphate buffer pH7.0 containing 10 mM cyanuric chloride. The reaction was allowed to proceed for 1 hour at room temperature and the coating was rinsed with distilled water and air-dried. Goat anti-mouse antibody was spotted onto such treated substrate and evaluated as described in Example 2.

The surface protein binding capacity was evaluated according to the ELISA protocol as described in Example 2. The results are shown in Table 2.

Example 4

This example illustrates the modification of coated gelatin using heterobifunctional crosslinkers to improve its surface protein binding capacity.

4-1: Gelatin was coated according to Example 1 and the coating was immersed in 0.01 M phosphate buffer pH7.0 containing 10 mM N-(γ-maleimidobutyryloxy) succinimide ester. The reaction was allowed to proceed for 1 hours at room temperature and the coating was rinsed with distilled water and air-dried.

Goat anti-mouse antibody was reduced in 0.05 M DTT and allowed to stand at room temp for 10 min. Immediately prior to use, the reduced antibody solution was extracted four times with ethyl acetate to remove DTT from sample.

Goat anti-mouse antibody was spotted onto such treated substrate surface and evaluated essentially as described in Example 2 except that cysteine was used instead of glycine in step 2 and 7. The results are shown in Table 2.

TABLE 2

| Sample ID | Spot density with 50 ng of goat anti-mouse IgG | Spot density with 25 ng of goat anti-mouse IgG | Spot density with 10 ng of goat anti-mouse IgG | Spot density with 0 ng of goat anti-mouse IgG, background density | Comments |
|---|---|---|---|---|---|
| 1-1 | 0.13 | N/A* | N/A* | 0.08 | Comparative |
| 3-1 | 0.52 | 0.31 | 0.28 | 0.11 | Invention |
| 3-2 | 0.57 | 0.48 | 0.32 | 0.06 | Invention |
| 3-3 | 0.62 | 0.38 | 0.36 | 0.16 | Invention |
| 4-1 | 0.74 | 0.64 | 0.6 | 0.1 | Invention |

*No spot signal can be detected at these levels of goat anti-mouse IgG. Treatment of gelatin surfaces with homobifunction and heterobifunction crosslinkers improved protein surface binding capacity and allowed lower laydown of detection antibody molecules (signals were readily detectable with 10 nono grams of proteins spotted on the modified surfaces).

Example 5

This example illustrates the non-specific binding to protein of coated gelatin surface.

A silicon wafer or glass was treated with 10% wt. NaOH solution in ethanol for 10 min and annealed at 580° C. for 30 min. A 1 wt. % 3-aminopropyltriethoxylsilane (APS, form Gelest Inc.) aqueous solution was prepared and adjusted to pH 3.5 by using acetic acid. After placing the treated wafer or glass in the APS solution, pH of the solution was adjusted to 5.5 with NaOH. The reaction was allowed for 1 hour, then the surface rinsed thoroughly with water, and dried in nitrogen. The APS layer grafted on glass or wafer surface was measured with ellipsometry (GAERTNER® L116B) and found to have a thickness of 8 Å. The gelatin and polyethylenimine (PEI) surfaces were further derived by first treating the APS surface with a 10 mM cyanic chloride (from Aldrich®) in acetonitrile solution for one hour, and then dipping the slides in 0.1% wt solutions of gelatin and PEI (from Aldrich®, MW ~2000) for over night. The surfaces were found to have bonded a layer of gelatin and PEI with the thickness of 47 Å and 30 Å, respectively.

The protein non-specific bonding to the three amine functional group containing surfaces was tested by soaking the APS, gelatin and PEI coated slides in a 100 μg/ml bovine serum albumin (BSA, from Sigma®) solution in pH=7 phosphate buffer solution for 60 min and rinse with water for 2 min. The amounts of BSA non-specifically adsorbed to the surfaces were determined by ellipsometry. The results are shown in Table 4:

Table 3: BSA Non-Specific Bonding to Amine Containing Surfaces of Gelatin, APS, and PEI

TABLE 3

| Gelatin | APS | PEI |
|---|---|---|
| 6 Å | 10 Å | 13 Å |

The results show that the gelatin surface has significantly lower non-specific bonding capacity than the other amine functional group containing materials. Note, for example, that the gelatin coated surface absorbs significantly less BSA than the amine coated surfaces.

The invention has been described in detail with particular reference to certain preferred embodiments thereof, but it will be understood that variations and modifications can be effected within the spirit and scope of the invention.

What is claimed is:

1. A gelatin-based substrate for fabricating protein arrays, the substrate comprising: a support having a coating thereon comprising gelatin and a trifunctional compound A—L—B affixed in said gelatin; wherein A is a functional group capable of interacting with the gelatin; L is a linking group capable of interacting with A and with B; and B is a functional group capable of interacting with a protein capture agent, wherein A may be the same or different from B.

2. The gelatin-based substrate of claim 1 wherein the interaction between the gelatin and A is a physical binding or a chemical reaction.

3. The gelatin-based substrate of claim 1 wherein the interaction between the protein capture agent and B is a physical binding or a chemical reaction.

4. The gelatin-based substrate of claim 1 wherein either A or B, or both, is aldehyde, epoxy, hydrazide, vinyl sulfone, succinimidyl ester, carbodiimide, maleimide, dithio, iodoacetyl, isocyanate, isothiocyanate, or aziridine.

5. The gelatin-based substrate of claim 1 wherein B is an affinity tag capable of interacting non-covalently with a protein capture agent that is to be immobilized onto the substrate.

6. The gelatin-based substrate of claim 1 wherein B is streptavidin, biotin, glutathione-S-transferase, glutathione, or histidine tags.

7. The gelatin-based substrate of claim 1 wherein L is a diradical of such a length that the shortest through-bond path between the ends that connect A to B is not greater than 10 atoms.

8. The substrate of claim 1 wherein the gelatin is alkaline pretreated.

9. The substrate of claim 1 wherein the gelatin is pig gelatin or fish gelatin.

10. The substrate of claim 1 wherein the gelatin coverage is 0.2 to 100 grams per square meter.

11. The substrate of claim 1 wherein the gelatin coverage is 10 to 50 grams.

12. A method of making a gelatin-based substrate for fabricating protein arrays comprising the steps of:
providing a support;
coating on the support a composition containing gelatin;
affixing to a surface of the gelatin a trifunctional compound A—L—B, wherein A is a functional group capable of interacting with the gelatin, L is a linking group capable if interacting with A and with B, and B is a functional group capable of interacting with a protein capture agent; wherein A may be the same or different from B, and wherein the trifunctional compound ALB is affixed while coating the gelatin on the substrate.

13. The method of claim 12 wherein the protein capture agent is antibody, protein scaffold, peptide, nucleic acid ligand, or a molecular imprinting polymer.

14. A method of making a substrate having a protein capture agent affixed onto a surface comprising the steps of:
providing a substrate comprising gelatin;
affixing in the gelatin a trifunctional compound A—L—B, wherein A and B are each independently selected from a functional group capable of interacting with the gelatin and a protein capture agent, and L is a linking group capable if interacting with A and with B; and
bringing said surface of the gelatin in contact with a protein.

15. A substrate comprising gelatin, a trifunctional compound A—L—B affixed in the gelatin, and a plurality of protein capture agents attached to the gelatin through the trifunctional compound A—L—B, wherein A and B are each independently selected from a functional group capable of interacting with the gelatin and a protein capture agent, and L is a linking group capable if interacting with A and with B.

16. The substrate of claim 15 wherein the protein capture agent is an antibody, protein scaffold, peptide, nucleic acid ligand, or a molecular imprinting polymer.

17. A method of making a gelatin-based substrate for fabricating protein arrays comprising the steps of:
providing a support;
coating on the support a composition containing gelatin;
affixing in the gelatin a trifunctional compound A—L—B, wherein A and B are each independently selected from a functional group capable of interacting with the gelatin and a protein capture agent, and L is a linking group capable if interacting with A and with B; wherein A may be the same or different from B, and wherein the trifunctional compound A—L—B is affixed after coating the gelatin on the substrate.

18. The method of claim 17 wherein the protein capture agent is antibody, protein scaffold, peptide, nucleic acid ligand, or a molecular imprinting polymer.

* * * * *